US011150005B2

(12) United States Patent
Sohn

(10) Patent No.: US 11,150,005 B2
(45) Date of Patent: Oct. 19, 2021

(54) ENDOTHERMIC TOWEL

(71) Applicant: Dae Up Sohn, Incheon (KR)

(72) Inventor: Dae Up Sohn, Incheon (KR)

( * ) Notice: Subject to any disclaimer, the term of this patent is extended or adjusted under 35 U.S.C. 154(b) by 227 days.

(21) Appl. No.: 14/694,554

(22) Filed: Apr. 23, 2015

(65) Prior Publication Data

US 2016/0061510 A1   Mar. 3, 2016

(30) Foreign Application Priority Data

Sep. 2, 2014  (KR) ................. 10-2014-0116384

(51) Int. Cl.
| | |
|---|---|
| *F25D 5/02* | (2006.01) |
| *A47K 10/02* | (2006.01) |
| *A61F 7/10* | (2006.01) |
| *A61F 7/02* | (2006.01) |
| *A61F 7/00* | (2006.01) |

(52) U.S. Cl.
CPC ............... *F25D 5/02* (2013.01); *A47K 10/02* (2013.01); *A61F 7/02* (2013.01); *A61F 7/10* (2013.01); *A61F 2007/0009* (2013.01); *A61F 2007/026* (2013.01); *A61F 2007/0214* (2013.01); *A61F 2007/0215* (2013.01)

(58) Field of Classification Search
CPC ......... F25D 5/00; F25D 5/02; A41D 2400/10; A41D 2400/20; A41D 2400/22; A42C 5/02; A42C 5/04
USPC .............................................................. 62/4
See application file for complete search history.

(56) References Cited

U.S. PATENT DOCUMENTS

| | | | | |
|---|---|---|---|---|
| 4,797,310 A | * | 1/1989 | Barby .................... | A47L 13/17 428/316.6 |
| 2005/0241093 A1 | * | 11/2005 | McKenzie .............. | A47L 13/16 15/209.1 |
| 2009/0172905 A1 | * | 7/2009 | Sohn ...................... | A47K 10/02 15/210.1 |
| 2012/0047619 A1 | * | 3/2012 | Lambertz ............... | A41D 27/28 2/69 |
| 2013/0125306 A1 | * | 5/2013 | Andrews ................. | A47G 9/06 5/417 |
| 2013/0198956 A1 | * | 8/2013 | Khan ...................... | A47G 9/04 5/498 |
| 2014/0109329 A1 | * | 4/2014 | Gummow ................ | A47L 1/15 15/104.93 |
| 2014/0150156 A1 | * | 6/2014 | Sprague ................. | A47K 10/02 2/69 |

FOREIGN PATENT DOCUMENTS

| | | |
|---|---|---|
| JP | 06-0316014 A | 11/1994 |
| JP | 09-170108 A | 6/1997 |

(Continued)

*Primary Examiner* — Elizabeth J Martin
*Assistant Examiner* — Nael N Babaa
(74) *Attorney, Agent, or Firm* — Novick, Kim & Lee, PLLC; Jae Youn Kim

(57) ABSTRACT

Provided is an endothermic towel which can react with moisture of a human body to cause an endothermic reaction, thereby removing thermal sensation and at the same time, rapidly drying moisture to give cool sensation to a user. The endothermic towel includes a towel body having an endothermic function; and a plurality of through-holes provided to the towel body in order to accelerate the endothermic function, so that the endothermic function may be optimized.

5 Claims, 4 Drawing Sheets

(56) References Cited

FOREIGN PATENT DOCUMENTS

| | | | |
|---|---|---|---|
| JP | 2000-095679 A | | 4/2000 |
| JP | 3074591 U | | 1/2001 |
| JP | 2004049857 A | * | 2/2004 |
| JP | 2004115964 A | * | 4/2004 |
| JP | 2004115964 A | * | 4/2004 |
| JP | 20044115964 A | * | 4/2004 |
| JP | 2005-187994 A | | 7/2005 |
| JP | 3175126 U | | 4/2012 |
| KR | 10-1999-0064559 A | | 8/1999 |
| KR | 2011-0138525 A | | 12/2011 |
| WO | 2005/068916 A1 | | 7/2005 |

* cited by examiner

ENDOTHERMIC TOWEL

BACKGROUND OF THE INVENTION

1. Field of the Invention

The present invention relates to an endothermic towel, and more particularly, to an endothermic towel which can react with moisture of a human body to cause an endothermic reaction, thereby removing thermal sensation and at the same time, rapidly drying moisture to give cool sensation to a user.

2. Description of the Related Art

In general, when exposed to sunlight at summer vacation spot, outdoor sports bleachers, an outdoor workshop, etc., a user wears a towel or facecloth wetted with water around the neck to feel cool sensation.

However, when the towel or facecloth wetted with water is used, the residual moisture remains on the skin so that the user feels unpleasant and the wetted towel or facecloth wets the clothes.

In addition, patches or cosmetic used as quasi-drugs contains a small amount of an ingredient, such as menthol, sorbitol or peppermint oil, to give cool sensation to the skin. However, although the ingredient can give freshness sensation to the skin, the ingredient does not actually reduce the temperature of skin and there are many restrictions to use it for a face because the ingredient may severely irritate the skin when a great amount of ingredients is applied to the face.

In addition, as a manner of giving cool sensation, a lotion which is melted when making contact with the skin of a user is well known. The heat to melt the lotion is gotten from the user skin. Since the lotion takes the heat from the user without any temperature changes related to the melting operation, the skin is cooled actually. That is, an endothermic material for giving cool sensation to the user has been developed.

Recently, in addition to the above-mentioned material, a towel (called cool towel) that uses a fabric made of PVC and has excellent absorptiveness has been developed and available in the market. The cool towel can reduce the temperature of a part of a body contacting therewith and circulating heated moisture to an outside of the fabric.

For example, as shown in FIG. 1, a towel, which is made of a fabric having a honeycomb structure capable of absorbing moisture of about 1.5 times as much as a commercial fabric to give cool sensation to the user, has been available in the market.

Meanwhile, the examples of a technique of giving cool sensation to the user by using an endothermic reaction are disclosed in the following document 1 to 3.

For example, a hood employing an absorptive material such as absorptive polymer, which is worn on the back of the head of a cheering person in order to block direct light and cool a wearing part by vaporization, is disclosed in Japanese Unexamined Patent Publication No. 1997-170108 (published on Jun. 30, 1997).

In addition, a cooling solution obtained by diluting perfume, cooling agent or alcohol including menthol or peppermint, which is impregnated into a main pocket part of clothes of a user in order to keep freshness sensation for a long time when the user plays a sport or works at an outdoor place, is disclosed in Japanese Unexamined Patent Publication No. 2000-095679 (published on Apr. 4, 2000).

In addition, an absorbent fibrous sheet, which contains one or more chemical agents that react exothermically endothermically when the sheet is subjected to an externally-applied non-thermal stimulus such that the temperature of the sheet increases or decreases by at least 1° C., is disclosed in PCT publication No. WO 2005/068916 (published on Jul. 28, 2005).

However, since the techniques described above use chemical or absorbent materials, it is troublesome to utilize the techniques. In addition, it is harmful to the human body when chemical or absorbent materials are frequently used or when the human body is exposed to such chemical or absorbent materials.

In addition, when the towel shown in FIG. 1 is used, the quantity of heat generated from the towel may be reduced, or the towel may be stretched or stink due to frequent use. That is, when the towel shown in FIG. 1 is reused repeatedly after washing the towel, the elasticity of the entire towel may be lowered so that the function of absorbing moisture may be deteriorated, that is, it is undesired to repeatedly reuse the towel.

In addition, when the towel shown in FIG. 1 is used between the skin and the cloth of a user, for example, between the neck and the shirt of the user, the towel may be pressed by the shirt so that the function of generating heat may be deteriorated, so the shirt may be wet.

In the structure shown in FIG. 1, it is inconvenient that a user must use the towel after visually recognizing and distinguishing the front and rear surfaces of the towel according to the exothermic and endothermic functions, of the towel.

In addition, the towel according to the related art is prepared in a dual structure, and gives unpleasant sensation to neighboring people when the moisture is removed from the towel by shaking or rotating the towel after the moisture is wrung out of the towel with hands to minimize a quantity of moisture absorbed by the towel such that the endothermic function is performed at the maximum.

Meanwhile, according to the related art, since the towel is fabricated in a dual structure or provides a seam for preventing strains from being unwound at an edge of the towel through a sewing scheme, the manufacturing cost is increased and the seam makes contact with the skin of the user so that unpleasant sensation may be given to a user.

SUMMARY OF THE INVENTION

The present invention is provided to solve the above problems, and therefore, an object of the present invention is to provide an endothermic towel capable of removing unpleasant sensation of a user.

Another object of the present invention is to provide an endothermic towel that does not give unpleasant feeling to neighboring people in use.

Still another object of the present invention is to provide an endothermic towel which can be simply fabricated so that the fabrication cost can be reduced.

Still another object of the present invention is to provide an endothermic towel that allows the user to be easily recognized in dark environment.

To achieve the objects, according to the present invention, there is an endothermic towel which reacts with moisture to cause an endothermic reaction to remove thermal sensation, which includes: a towel body having an endothermic function; and a plurality of through-holes provided in the towel body in order to accelerate the endothermic function.

The towel body may be flexible in a longitudinal direction.

The through-holes may be aligned in line with each other in the longitudinal direction.

The though-holes may be offset from each other in the longitudinal direction.

The endothermic towel may further include a light emitting part provided on a surface of the towel body.

The light emitting part may be provided in a straight structure.

The light emitting part may be provided in a moiré structure.

An edge of the towel body may be formed without a seam member.

The towel body may be formed of a single fabric.

The towel body may be dyed with a fluorescent dye.

As described above, the endothermic towel according to the present invention may be flexible only in a longitudinal direction due to the through-holes provided in the towel body, so that the endothermic function is accelerated.

In addition, according to the endothermic towel of the present invention, since moisture is removed from the towel body by shaking the towel with both hands of a user, those around the user may not feel unpleasant.

In addition, according to the endothermic towel of the present invention, the towel body is formed of a single fabric without providing any seam members on the edge of the towel body, so that the fabrication process for the seam members may be omitted, thereby reducing the fabrication cost.

In addition, according to the endothermic towel of the present invention, the light emitting part is provided on the surface of the towel body and the towel body is dyed with the fluorescent dye, so that the user wearing the towel body can be easily recognized in dark environment.

DETAILED DESCRIPTION OF THE INVENTION

The above and other objects and features of the present invention will be more apparent from the description of the specification and the accompanying drawings.

Hereinafter, the configuration of the present invention will be described with reference to the drawings.

Figure 1:
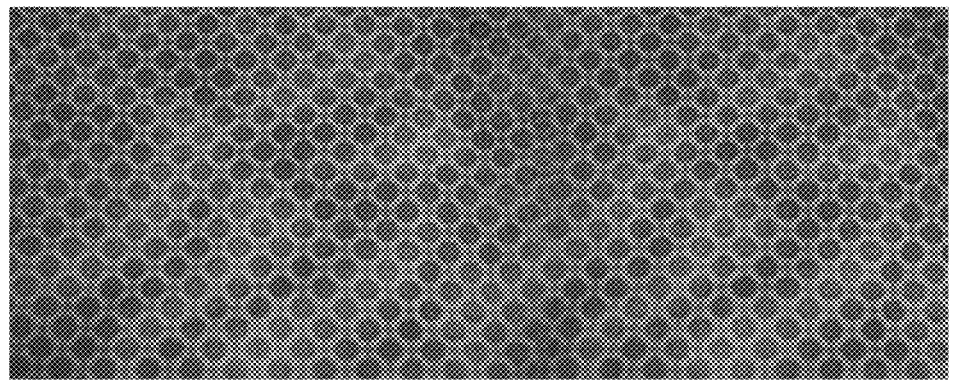
FIG. 1 is a photograph of a structure of an endothermic towel according to the related art.
Figure 2:
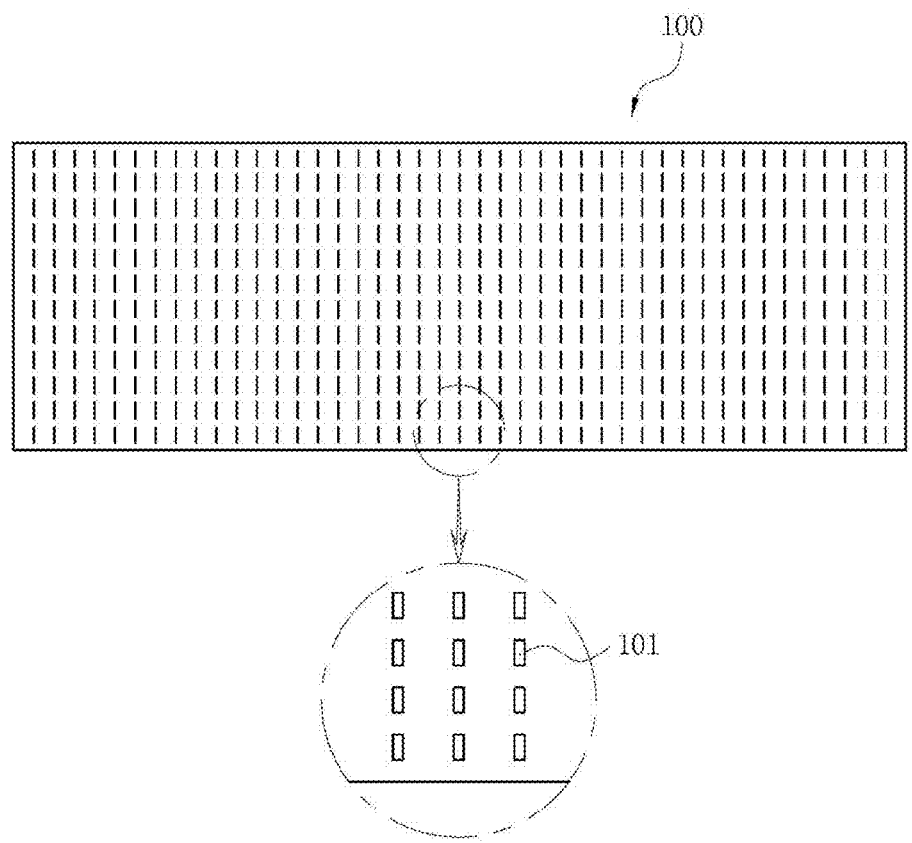
FIG. 2 is a plane view showing an endothermic towel according to a first embodiment.

FIG. 2 is a plane view showing an endothermic towel according to a first embodiment.

As shown in FIG. 2, the endothermic towel according to the first embodiment of the present invention, in which an endothermic reaction occurs to remove thermal sensation, includes a towel body having an endothermic function, and a plurality of through-holes 101 provided to the towel body in order to accelerate the endothermic function.

The towel body 100 is formed of a single fabric having high absorptiveness and elasticity and prepared to be elasticated in a longitudinal direction. That is, the towel body 100 is freely elasticated in the longitudinal direction in FIG. 2 but is not almost elasticated in the traversal direction in FIG. 2.

As shown in FIG. 2, the though-holes 101 formed in the towel body 100 according to the present invention are formed in a substantially rectangular shape, respectively and are aligned in line with each other in the longitudinal direction. Since the number of through holes in the longitudinal direction is greater than that in the traversal direction, the elasticity is more effective in the longitudinal direction. As described above, since the through-holes 101 are provided in the towel body 100, the heat absorbed by the towel body 100 may be effectively radiated through the through-holes 101.

The through-holes 101 may be formed when the towel body 100 is woven, or may be formed through a punching or laser processing scheme after the towel body 100 is woven.

In addition, as shown in FIG. 2, any seam members are provided to an edge of the towel body 100 according to the present invention, the towel may be completed by cutting the towel body 100 by a constant length and width.

Therefore, as compared with that according to the related art, the towel according to the present invention may be formed through a simple process, so that the fabrication cost may be reduced. In addition, when the towel makes contact with the skin of a user, the seam member may prevent the user from feeling unpleasant sensation.

Meanwhile, the towel body 100 is dyed with a fluorescent dye, so that the user may be easily recognized at a dark work area at night. That is, when a user wears the towel body 100 of the present invention, for example, around his neck in a space in which it is difficult to recognize the user without lighting, one may recognize the user due to the light emission of the towel body 100, so that an unexpected accident may be prevented from occurring.

As shown in FIG. 2, similarly to a conventional towel, the towel according to the present invention is formed in a substantially rectangular shape, but the present invention is not limited thereto and the towel may be formed in a square shape as a handkerchief or in a triangular or circular shape according to the purpose of use. In addition, a size of the towel may be adjusted according to the purpose of use, but the present invention is not limited thereto.

Preferably, a textile product, in which an ingredient, such as xylitol, erythritol or the mixture thereof, giving endothermic effect and freshness sensation the towel body 100 is embedded, may be used as a material of the towel body 100. Thus, since the towel according to the present invention contains an ingredient of xylitol, an exothermic property of the towel may be more enhanced.

As a material of the towel body 100, a textile product containing a coffee ingredient having a deodorization function may be used. Thus, since the towel body 100 has the deodorization function, even when the towel is repeatedly used, the stench of the towel may be reduced.

A method of using the towel of the present invention described above will be described with reference to FIGS. 3 and 4.

Figure 3:
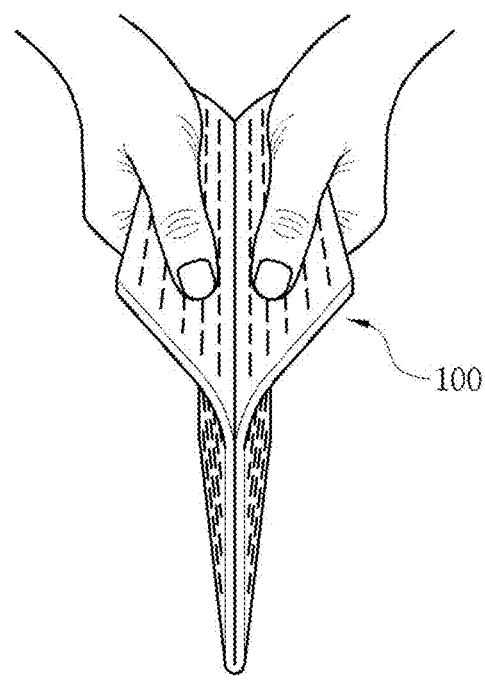
FIGS. 3 and 4 are views illustrating an example of using an endothermic towel according to an embodiment.
Figure 4:
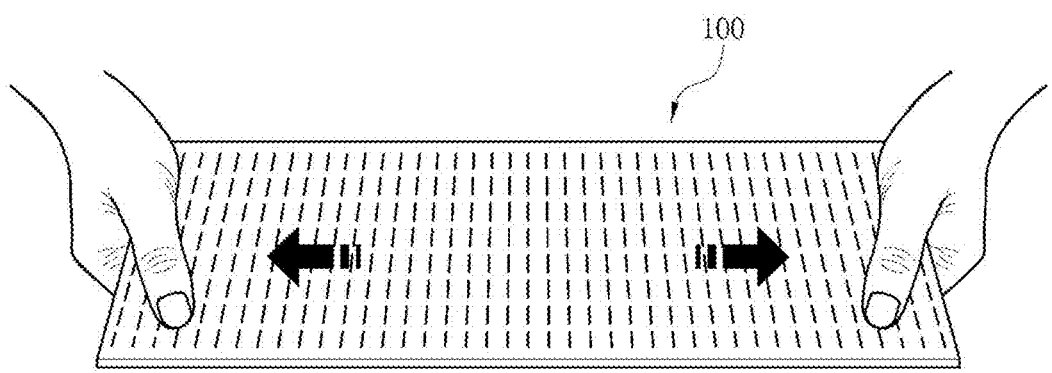

FIGS. 3 and 4 are views illustrating an example of using an endothermic towel according to an embodiment.

As shown in FIG. 3, when excessive moisture exists in the towel body 100 of the present invention having the endothermic function, the excessive moisture may be removed from the towel body 100 by stretching the towel body 100 at the front of a user as shown in FIG. 4 while gripping both ends of the towel body 100 depicted in FIG. 2 with hands.

That is, the function of vaporizing moisture of the towel body 100 may be optimized by repeating the states depicted in FIGS. 3 and 4, so that the clothes of a user may be prevented from being wet.

The excessive moisture of the towel body 100 falls down at the front of a user through the though-holes 101 by stretching the towel body 100 in the longitudinal direction, so that the moisture is prevented from being scattered to people neighboring on the user, so the towel does not cause damage to those around a user in use.

Next, a towel according to another embodiment of the present invention will be described with reference to FIGS. 5 to 7.

Figure 5:
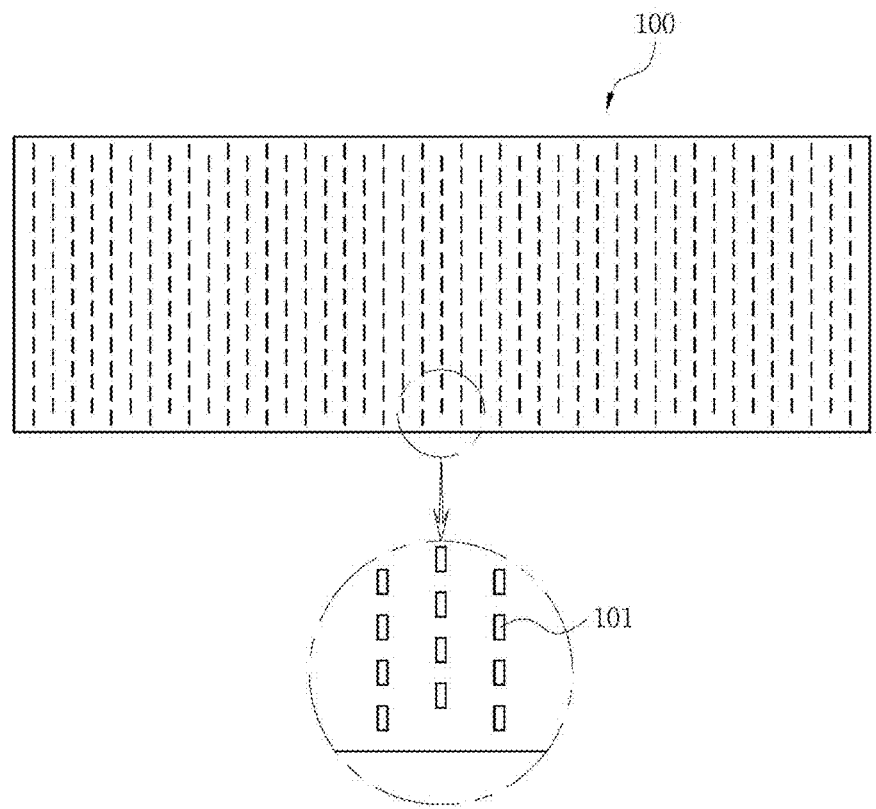
FIG. 5 is a plane view showing an endothermic towel according to a second embodiment.

FIG. 5 is a plane view showing an endothermic towel according to a second embodiment. FIG. 6 is a plane view showing an endothermic towel according to a third embodiment. FIG. 7 is a plane view showing an endothermic towel according to a fourth embodiment.

According to the second embodiment, as shown in FIG. 5, the through-holes 101 are offset from each other in the longitudinal direction to cross each other. Since the elements of the towel according to the second embodiment are equal to those of the towel according to the first embodiment except for the structure of the through-holes, the details will be omitted.

According to the second embodiment, since the through-holes 101 are offset from each other in the longitudinal direction to cross each other, differently from the first embodiment, the stretch of the towel in the longitudinal direction may be accelerated while the towel is prevented from being stretched in the traversal direction. Thus, the function shown in FIGS. 3 and 4 may be more effectively implemented.

Figure 6:
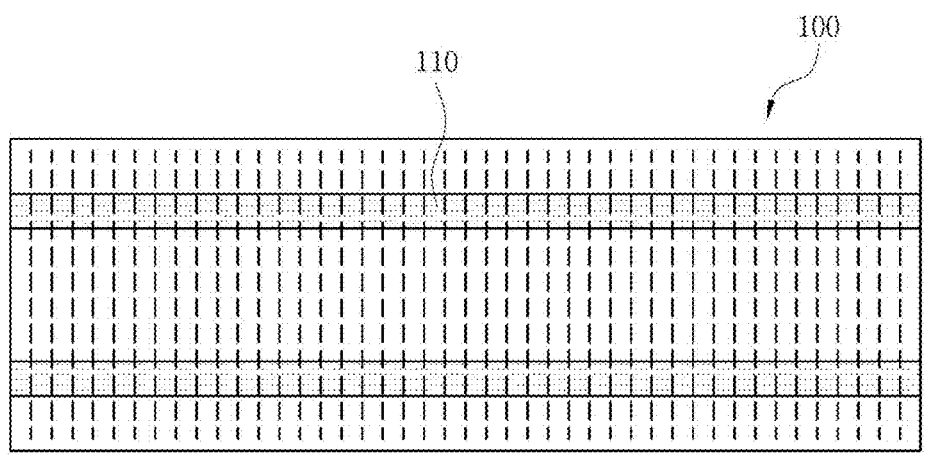
FIG. 6 is a plane view showing an endothermic towel according to a third embodiment.

According to the third embodiment, as shown in FIG. 6, a light emitting part 110 is provided on the surface of the towel body. Since the elements of the towel according to the third embodiment are equal to those of the towel according to the first embodiment except for the structure of the light emitting part 110, the details will be omitted.

Differently from the towel body 100 according to the first embodiment, the towel body 100 according to the third embodiment is not dyed with a fluorescent dye, but the light emitting part 110 is provided in a dual-straight structure, so that the fabricating cost of may be reduced as compared with the first embodiment.

In addition, the light emitting part 110 having the dual-straight structure has been described in the third embodiment, but the present invention is not limited thereto and the light emitting part 110 may be formed in a single straight structure or multi-straight structure. In addition, although the light emitting part 110 formed in a longitudinal direction has shown in FIG. 6, the present invention is not limited thereto and the light emitting part 110 may be formed in a traversal direction.

Figure 7:
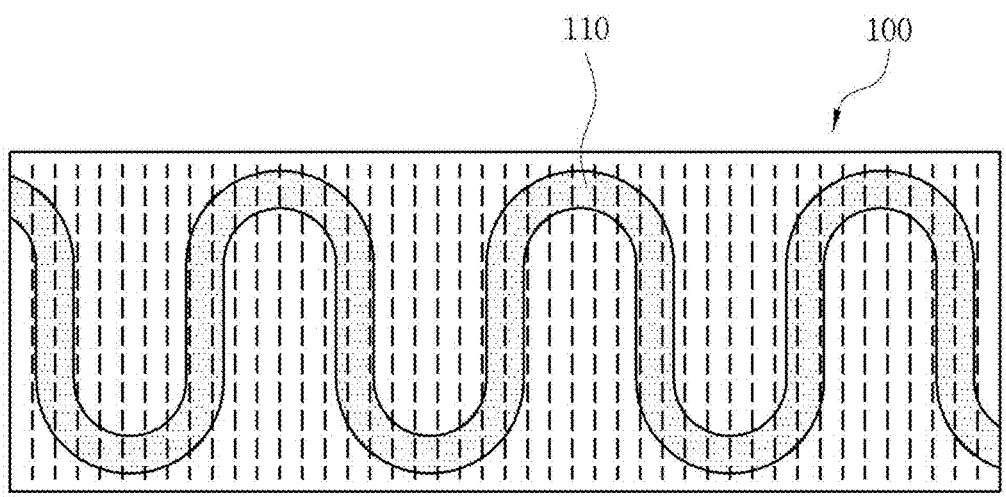
FIG. 7 is a plane view showing an endothermic towel according to a fourth embodiment.

According to the fourth embodiment, as shown in FIG. 7, a light emitting part is provided on the surface of the towel body in a moiré structure. Since the elements of the towel according to the fourth embodiment are equal to those of the towel according to the third embodiment except for the structure of the light emitting part 110, the details will be omitted.

Differently from the towel body 100 according to the first embodiment, the towel body 100 according to the third embodiment is not dyed with a towel body 100 and the light emitting part 110 is provided on the towel body 100 in the moiré structure, so that the fabrication cost of the fourth embodiment may be reduced as compared with that of the first embodiment.

In addition, the light emitting part 110 having the moiré structure has been described in the fourth embodiment, but the present invention is not limited thereto and the light emitting part 110 may be formed in a sequence of a single structure such as a star shape, a circular shape or a polygonal shape.

Although an exemplary embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. An endothermic towel which reacts with moisture to cause an endothermic reaction to remove thermal sensation, the endothermic towel comprising:
   a towel body composed of a single fabric having an endothermic function; and
   a plurality of through-holes provided in the towel body in order to accelerate the endothermic function, each of the plurality of through-holes being in a rectangular shape,
   wherein the number of the plurality of through-holes in a longitudinal direction of the towel is greater than that in a traversal direction of the towel,
   wherein each of the plurality of rectangular shaped through-holes has a horizontal side parallel to the longitudinal direction and a vertical side parallel to the traversal direction, and the horizontal side is shorter than the vertical side, and
   wherein an edge of the towel body is formed without a seam member,
   wherein the through-holes include a first line of through-holes having a first through-hole and a second through hole and a second line of through-holes having a first through-hole and a second through-hole, and
   wherein the first through-hole of the first line of through-holes is offset from that of the second line of through-holes, and the second through-hole of the first line of through-holes is offset from that of the second line of through-holes in the longitudinal direction.

2. An endothermic towel which reacts with moisture to cause an endothermic reaction to remove thermal sensation, the endothermic towel comprising:
   a towel body composed of a single fabric having an endothermic function; and
   a plurality of through-holes provided in the towel body in order to accelerate the endothermic function, each of the plurality of through-holes being in a rectangular shape, wherein the number of the plurality of through-holes in a longitudinal direction of the towel is greater than that in a traversal direction of the towel; and
   a light emitting part provided on a surface of the towel body,
   wherein each of the plurality of rectangular shaped through-holes has a horizontal side parallel to the longitudinal direction and a vertical side parallel to the traversal direction, and the horizontal side is shorter than the vertical side,
   wherein an edge of the towel body is formed without a seam member, and
   wherein the light emitting part is provided in a straight structure, wherein the through-holes include a first line of through-holes having a first through-hole and a second through hole and a second line of through-holes having a first through-hole and a second through-hole, and wherein the first through-hole of the first line of through-holes is offset from that of the second line of through-holes, and the second through-hole of the first line of through-holes is offset from that of the second line of through-holes in the longitudinal direction.

3. An endothermic towel which reacts with moisture to cause an endothermic reaction to remove thermal sensation, the endothermic towel comprising:

a towel body composed of a single fabric having an endothermic function; and a plurality of through-holes provided in the towel body in order to accelerate the endothermic function, each of the plurality of through-holes being in a rectangular shape, wherein the number of the plurality of through-holes in a longitudinal direction of the towel is greater than that in a traversal direction of the towel; and a light emitting part provided on a surface of the towel body, wherein each of the plurality of rectangular shaped through-holes has a horizontal side parallel to the longitudinal direction and a vertical side parallel to the traversal direction, and the horizontal side is shorter than the vertical side, wherein an edge of the towel body is formed without a seam member, and wherein the light emitting part is provided in a moiré structure, wherein the through-holes include a first line of through-holes having a first through-hole and a second through hole and a second line of through-holes having a first through-hole and a second through-hole, and wherein the first through-hole of the first line of through-holes is offset from that of the second line of through-holes, and the second through-hole of the first line of through-holes is offset from that of the second line of through-holes in the longitudinal direction.

4. The endothermic towel of claim 1, wherein the towel body is dyed with a fluorescent dye.

5. The endothermic towel of claim 1, wherein the towel body includes at least one of xylitol, erythritol, or a combination thereof for the endothermic function.

* * * * *